US010570376B2

(12) United States Patent
Peterka et al.

(10) Patent No.: US 10,570,376 B2
(45) Date of Patent: Feb. 25, 2020

(54) METHOD FOR INFLUENZA VIRUS PURIFICATION

(71) Applicants: BIA SEPARATIONS D.O.O., Ljubljana (SI); AVIR Green Hills Biotechnology Development Trade AG, Vienna (AT)

(72) Inventors: Matjaz Peterka, Ljubljana (SI); Ales Strancar, Ajdovscina (SI); Marko Banjac, Ajdovscina (SI); Petra Kramberger, Domzale (SI); Elisabeth Roethl, Vienna (AT); Thomas Muster, Vienna (AT)

(73) Assignees: BIA SEPARATIONS D.O.O., Ljubljana (SI); BAXTER HEALTHCARE SA, Glattpark (Opfikon) (CH)

(*) Notice: Subject to any disclaimer, the term of this patent is extended or adjusted under 35 U.S.C. 154(b) by 0 days.

(21) Appl. No.: 14/791,691

(22) Filed: Jul. 6, 2015

(65) Prior Publication Data
US 2016/0002606 A1   Jan. 7, 2016

Related U.S. Application Data

(63) Continuation of application No. 12/309,135, filed as application No. PCT/EP2007/056890 on Jul. 6, 2007, now abandoned.

(60) Provisional application No. 60/830,339, filed on Jul. 13, 2006.

(30) Foreign Application Priority Data

Jul. 11, 2006  (EP) ..................... 06116979

(51) Int. Cl.
| *C12N 7/00* | (2006.01) |
| *A61K 39/145* | (2006.01) |
| *B01D 15/36* | (2006.01) |
| *B01D 15/42* | (2006.01) |
| *B01D 36/00* | (2006.01) |

(52) U.S. Cl.
CPC .............. *C12N 7/00* (2013.01); *A61K 39/145* (2013.01); *B01D 15/363* (2013.01); *B01D 15/426* (2013.01); *B01D 36/003* (2013.01); *C12N 2760/16021* (2013.01); *C12N 2760/16034* (2013.01); *C12N 2760/16051* (2013.01)

(58) Field of Classification Search
CPC ........... C12N 7/00; C12N 2760/16151; C12N 2760/16051; C12N 2760/16251; C12N 7/02; C12N 2760/16034; C12N 2760/16021; B01D 36/003; B01D 15/426; B01D 15/363; A61K 39/145
See application file for complete search history.

(56) References Cited

U.S. PATENT DOCUMENTS

2013/0164821 A1*  6/2013  Faber ................. B01D 15/1871
                                                435/239

FOREIGN PATENT DOCUMENTS

| EP | 0171086 | 2/1986 |
| EP | 0171086 A2 * | 2/1986 | ........... A61K 39/145 |

OTHER PUBLICATIONS

GE Healthcare. Ion Exchange Chromatography & Chromatofocusing: Principles and Methods. Apr. 15, 2004. https://www.sigmaaldrich.com/content/dam/sigma-aldrich/docs/Sigma-Aldrich/General_Information/1/ge-ion-exchange-chromatography.pdf.*
Morenweiser R. Downstream processing of viral vectors and vaccines. Gene Ther. Oct. 2005;12 Suppl 1:S103-10.*
Podgornik A, et. al. Biotechnol Annu Rev. 2005;11:281-333.*
Roldão A, Mellado MC, Castilho LR, Carrondo MJ, Alves PM. Virus-like particles in vaccine development. Expert Rev Vaccines. Oct. 2010;9(10):1149-76.*
Michen B, Graule T. Isoelectric points of viruses. J Appl Microbiol. Aug. 2010;109(2):388-97. Epub Jan. 22, 2010.*
Saksule A. Purification and Recovery of Infectious Virus Particles Using Osmolyte Flocculation. Master's Thesis, Michigan Technological University, 2016.*
CIM Trademark of BIA Separations. Trademark Details and registration information. Registration date Dec. 17, 2002.
Strancar et al. 1998. Convective Interaction Media: Polymer-Based Supports for Fast Separation of Biomolecules, LC-GC Int. 11:660-669.
Kramberger et al. Purification of viruses on monithic chromatographic supports: ToMV case study, 2005.
Branovic et al. Purification of plasmid DNA and concentration viruses on monoliths. International Symposium on the Separation of Proteins, Peptides, and Polynucleotides (ISPPP); Nov. 5-8, Lubijan, Slovenia.
Kramberger et al. Monolithic Chromatographic Columns—The media of choice for purification an Concentration of Viruses. 2005.

(Continued)

*Primary Examiner* — Rachel B Gill
(74) *Attorney, Agent, or Firm* — Jacobson Holman PLLC

(57) ABSTRACT

A process for the purification of influenza virus or derivative thereof requires providing a source of influenza virus or derivative thereof, optionally subjecting the source to a pre-purification step, followed by subjecting the source to at least one chromatographic step on chromatographic material selected from the group consisting of porous particles having mean pore sizes of at least 20 nm, perfusion particles, gel-in-a-shell particles, tentacle like particles, membrane adsorbers, and monoliths, and collecting fractions eluted from the chromatographic material that contain the influenza virus or derivative thereof, excluding sulfuric ester of cellulose or cross-linked polysaccharides.

10 Claims, 7 Drawing Sheets

(56) References Cited

OTHER PUBLICATIONS

Kramberger et al. Chromatography using short layer monolithic columns—Method of choice for large scale virus purification, 2004.
BIA Separations enabling new generation biotherapeutics dated Apr. 2013. http://transmedri.uniri.hr/files/AlesS_About%20BIA%Separations%20%April%202013.pdf.
BIA Separations. Home/Education/Poster/Viruses & VLPs. http://www.biaseparations.com/education/posters/viruses-vips. accessed Dec. 22, 2014.
Kramberger et al. Concentration of plant viruses using monolithic chromatography supports. J. Virol Methods, Sep. 1, 2004:120(1):51-7.
Branovic et al. Application of short monolithic columns for improved detection of viruses, J. Virol Methods. Jun. 30, 2003;110(2):163-71.
Monoliths seen to revitalized Bioseparations. Genetic Engineeric and Biotechnology New. Oct. 1, 2006. http://www.genengnews.com/gen-articles/monoliths-see-to-revitalize-biaseparations/1906/.
Barut et al, Convective interaction media short monolithic columns: enabling chromatographic supports for the separation and purification of large biomolecules. J. Sep Sci. Oct. 2005;28(15):1876-92.
Urbas et al, Reversed phase monolithic analytical columns for the determination of HA1 subunit of influenza virus haemagglutinin. J. Chromatogr, A Apr. 29, 2011;1218(17)2432-7. Epub Dec. 28, 2010.
Bakry et al. Silica particles encapsulated poly(styrene-divinylbenzene) monolithic stationary phases for micro-high performance liquid chromatography. J. Chromatogr A. Nov. 3, 2006;1132(1-2):183-9 Epub. Aug. 22, 2006.
Reimer et al. Influenza virus purification with the zonal ultracentrifuge. Science. Jun. 3, 1966;152(3727):1379-81.
Transfiguracion et al. Size-exclusion chromatography purification of high-titer vesicular stomatitis virus G glycoprotein-psuedotyped retrevectors for cell and gene therapy applications. Hum Gene Ther. Aug. 10, 2003;14(12):1139-53.
Nayak et al. Downstream processing of MDCK cell-derived equine influenza virus. J. Chromatogr B Analyt Technol Biomed Life Sci. Sep. 5, 2005;823(2):75-81.
Genzel et al. Serum-free influenza virus production avoiding washing steps and medium exchange in large-scale microcarrier culture. Vaccine. Apr. 12, 2006;24(16):3261-72 Epub Jan. 19, 2006.
Kramberger et al. Application of monolithic columns for the fast separation of nanoparticles. American biotechnology laboratory, Dec. 2003 (Dec. 2003), pp. 27-28.
Gagnon et al, Monoliths seen to revitalize bioseparations. Genetic Engineering New, vol. 26, No. 17, Oct. 2006 (Oct. 2006) http://www.biaseperations.com/Library/pdf/GR766.pdf, retrieved on Dec. 11, 2006.
Infectious, Merriam-Webster's Medical Dictionary, https://www.ucsfhealth.org/dictionary, © 2017 Merriam-Webster, Incorporated.
Branovic et al, Application of short monolithic columns for improved detection of viruses. J. Virol. Meth. vol. 110, pp. 163-171, http://dx.doi.org/10.1016/S0166-0934(03)00125-3, 2003.
Kramberger et al. Application of monolithic columns for the fast separation of nanoparticles. American Biotechnology Laboratory, p. 27-28, http://www.biaseparations.com/component/hikashop/product/458-application-of-monolithic-columns-for-the-fast-separation-of-nanoparticles, Dec. 2003.
Merhar et al. Methacrylate monoliths prepared from various hydrophobic and hydrophilic monomers: Structural and chromatographic characteristics. Journal of Separation Science, vol. 26, No. 3-4, pp. 322-330, https://doi.org/10.1002/jssc.200390038, Mar. 2003.

\* cited by examiner

METHOD FOR INFLUENZA VIRUS PURIFICATION

The invention pertains to a process for the purification of influenza virus or derivative thereof, a process for the manufacturing of influenza virus or its derivative, a fraction of influenza virus or derivative thereof, a vaccine as well as a vector comprising the influenza virus or its derivative.

FIELD OF THE INVENTION

The present invention relates to the purification of different quantities of influenza virus or derivative thereof. In particular, the invention provides a quick, efficient and scalable process for the purification of commercial quantities of influenza virus which can be applied for human usage e.g. prophylactic application such as vaccination.

BACKGROUND OF INVENTION

Influenza viruses belong to the family Orthomyxoviridae and are separated into types A, B and C according to antigenic differences. Influenza A and B viruses are important respiratory pathogens, although influenza A viruses are the main cause of epidemics with high mortality rate.

Influenza viruses have a segmented, single-stranded RNA genome of negative polarity. The genome of influenza A viruses consist of eight RNA molecules encoding eleven (some influenza A strains ten) protein. The viral envelope is composed of a lipid bilayer on a layer of matrix protein (M1). Embedded in the lipid bilayer are glycoproteins hemagglutinin (HA) and neuraminidase (NA), which are responsible for virus attachment and penetration into the cell, and release of progeny virus from the infected cells, respectively. Both proteins also determine the subtypes of the influenza A viruses. High mutation rates and frequent genetic reassortment due to the segmented genome, contribute to great immunological variability, particularly of the HA and NA antigens of influenza A viruses. Type B viruses do not exhibit the same degree of antigenic variation and are primarily childhood pathogens, which can occasionally cause epidemics of the same severity as type A.

The incubation time for influenza ranges from 1 to 5 days. Clinical onset is characterised by abrupt fever, headache, malaise and myalgias. Systemic symptoms usually last for 3 days. Although precise data on influenza associated deaths are not available for all countries, in the United States influenza associated deaths range between 30 and 150 per 100000 population aged over 65.

During influenza epidemics attack rates of 1%-5% are most common, but the attack rate may reach 40%-50%. Economic impact of influenza epidemic or even pandemic can therefore be tremendous. Vaccination was recognised as the best approach to limit the epidemics and its harmful effects.

Since introduction in 1940s vaccines based on virus material cultured in chicken eggs have been found to be clearly effective against influenza infection and have resulted in a significant fall in the mortality rate of high risk population. Initially vaccines were highly contaminated by egg derived components and were highly pyrogenic and lacking in efficacy. To overcome problems many different purification techniques and methods for purification of influenza virus were tested. Veerarghavan and Sreevalsan (1961) compared several different methods of concentration and purification of influenza virus and found that two cycles of aluminium phosphate treatment was the best method, followed by ultracentrifugation, erythrocyte adsorption, single cycle aluminium phosphate treatment and finally the zinc oxide method. Early attempts of small scale chromatographic purification of influenza virus on calcium phosphate and on agarose-gel columns were reported in 1960s (Pepper, 1967) but infectivity of the virus was not determined during the experiment. Wallis et al (1972) have shown that influenza virus can be adsorbed on insoluble polyelectrolytes at low pH values under 6.0 and subsequently eluted at high pH. Since influenza virus is pH sensitive and infectivity of purified virus was not determined, applicability of this method for purification of infective influenza virus is not known. Polyethylene glycol precipitation, followed by gel permeation chromatography through controlled pore glass beads was also tested for influenza purification and compared to density gradient procedures (Heyward et al., 1977). The time required for density gradient procedures was tenfold greater than for combination of precipitation and gel permeation chromatography and the purity of virus obtained by both methods was similar. Sagar et al. (1980) used positively charged Zeta Plus filters for influenza virus concentration but for purification further steps are needed as suggested by authors.

U.S. Pat. No. 3,632,745 describes the purification of influenza viruses by dialysing a suspension of the virus against water containing bivalent metallic cations e.g. magnesium. U.S. Pat. Nos. 3,485,718 and 3,547,779 both disclose the use of barium sulphate in the purification of influenza virus. U.S. Pat. No. 3,478,145 discloses the use of calcium phosphate in the purification of influenza virus. U.S. Pat. No. 3,874,999 describes a process consisting of different centrifugation steps, precipitation (with $MgSO_4$), ultra filtration and dialysis. EP-A-0171086 disclose a method for purification of influenza virus with column chromatography using a sulphuric acid ester of cellulose or of a crosslinked polysaccharide. The patent application discloses a purification of influenza virus only from allantoic fluid and does not address virus recovery in terms of virus infectivity which remains unknown. After adsorption of the virus to the column and a washing step, the virus is eluted from the column with buffer containing high NaCl concentration (1.49 M) which influences virus infectivity and lowers recovery of infectious virus. The method is based on a particle support exhibiting low dynamic binding capacity for virus particles which in addition strongly depends on the flow rate. These properties influences down stream process significantly, since large column dimensions are needed and only a low flow rate can be used, all resulting in rather low productivity of the process.

U.S. Pat. No. 6,008,036 discloses a general method for purifying viruses from a cell line culture by chromatography. The disclosed method comprises an ion exchange chromatography step followed by a cation exchange chromatography step and optionally a metal-binding affinity chromatography step.

A major breakthrough in influenza purification was the development of the zonal ultracentrifuge (Reimer et al., 1966). This technology revolutionized the purification process and industrial production of influenza and also other viral vaccines. Up to date, it remains the basis for the down stream process of influenza virus vaccines. Usually purification of influenza virus from allantoic fluids consists of clarification by centrifugation, concentration by ultra filtration and purification by ultra centrifugation. These current methods for the purification of influenza viruses are cumbersome and do not easily allow fast large scale production of virus stocks for vaccines of requested purity.

New influenza epidemics and pandemic are likely to occur in the future and current egg-based vaccine production technology seems to be unable to respond to a pandemic crisis. Thus, a system that can rapidly produce new influenza vaccine is needed. One such approach is a cell culture-based process which can be easily scaled up. But the existing purification of influenza virus vaccine cannot follow this demand. Recently, scalable influenza virus purification process comprising of depth filtration, inactivation, ultra filtration and gel filtration was also described (Prasad Nayak et al, 2005). Since virus was inactivated, applicability of this process for purification of infective influenza virus remains unknown.

Thus, there is still a need for a fast, scalable, efficient and inexpensive down stream process to purify influenza viruses for vaccines or any other application requiring pure, immunogenic and/or infective virus. The present invention discloses such a process.

SUMMARY OF INVENTION

The present invention is directed to a process for the purification of influenza virus or derivative thereof comprising the steps of providing a source having influenza virus or derivative thereof, optionally subjecting the source to a pre-purification step, followed by at least one chromatographic step on porous particles having mean pore sizes of at least 20 nm, perfusion particles, gel-in-a-shell particles, tentacle like particles, membrane adsorbers, and monoliths followed by collecting eluting influenza virus or derivatives thereof containing fractions with the proviso that sulfuric ester of cellulose or of cross-linked polysaccharides are excluded.

In an embodiment of the present invention the at least one further chromatographic step is performed on materials selected from the group consisting of porous particles having mean pore sizes of at least 20 nm, perfusion particles, gel-in-a-shell particles, tentacle like particles, membrane adsorbers, and monoliths.

The term tentacle like particles is well-known to the skilled person. Typical materials falling into this category are disclosed in EP-A-0337144. Also the term gel-in-a-shell particles is a term used in the art. For example, materials produced according to the gel-in-a-shell technology comprise a structure developed from a hyperformance hydrogel which is polymerized in large pores of a solid support such as for example a ceramic support. The support can also be produced from organic materials. Such configurations are for example disclosed in U.S. Pat. Nos. 5,268,097 or 5,234,991.

EP-A-0337144 refers to materials comprising a primary or secondary aliphatic hydroxyl group-containing support coated with at least one covalently bounded polymer by graft polymerization.

These media are commercialized as FRACTOGEL® (chromatography resin) EMD and FractoPrep®, maybe there are some others. These names are not mentioned in EP-A-0337144.

U.S. Pat. No. 5,268,097 refers to passivated porous solid supports, exhibiting high porosity, physical rigidity, high charge density, high flow rates and chemical stability. Passivated porous solid supports are stabilized against leaching under harsh environmental conditions by the application of a thin, protective polymeric coating atop their porous surfaces and that are characterized by a reversible high sorptive capacity substantially unaccompanied by non-specific adsorption of or interaction with bio-molecules. Commercialized as HyperD®, U.S. Pat. No. 5,234,991 refers to porous mineral support coated with an aminated polysaccharide polymer having a cationic character.

The term perfusion particles is also well-known in the art. Materials falling into this category are disclosed in U.S. Pat. Nos. 5,384,042, 5,552,041, 5,605,623, and 5,833,861 and are commercially available under the tradename POROS®.

U.S. Pat. Nos. 5,384,042, 5,552,041, 5,605,623, and 5,833,861 disclose matrices defined by first and second interconnected sets of pores and a high surface area for solute interactions in fluid communication with the members of the second set of pores. The first and second sets of pores are embodied, for example, as the interstices among particles and throughpores within the particles. The pores are dimensioned such that, at high fluid flow rates, convective flow occurs in both pore sets, and the convective flow rate exceeds the rate of solute diffusion in the second pore set.

These references as well as EP-A-0337144 are incorporated by reference herewith.

Furthermore, the present invention is directed to a process for the manufacturing of influenza virus comprising the steps of infecting cells with influenza virus, propagating the influenza virus in the cells, harvesting of the influenza viruses, and subjecting the harvested influenza virus or derivative thereof to a purification according to the process of the invention of purification of influenza virus or derivative thereof.

The process of the invention is suitable for the purification of laboratory and commercially useful quantities of influenza virus, e.g. either for vaccine or as viral vector use. The invention advantageously avoids problems associated with existing methods of purifying influenza virus and relies on ultra filtration and chromatographic techniques which enable simple scale up of the process.

The process of the invention accomplishes to purify influenza virus particles from cell lysate employing optionally ultra filtration, followed by a step in which virus is bound and subsequently eluted from the chromatographic support and a final step in which virus is purified out of remaining impurities and at the same time changing the buffer in which virus was prior to the step. The present purification process greatly reduces the level of contaminants from influenza virus sample and enables the application of purified influenza virus for human use.

The purification process of the present invention allows for the use of wide variety of commercially available ultra filtration devices and chromatographic supports known to be useful in separation of biological material either on laboratory or on industrial scale level. Ultra filtration devices can include flat sheet or hollow fibre design, and chromatographic supports include different basic material (natural and synthetic polymers) with different active groups and different types of the bed (porous particles, membranes, monoliths).

The process of the invention is advantageous because due to the mild conditions the potency of the influenza virus, such as immunogenicity and/or infectivity can be substantially maintained. According to a preferred embodiment of the invention, the elution buffer comprises ≤1M NaCl, preferably ≤0.8M NaCl, preferably ≤0.5M NaCl, alternatively ≤0.3M NaCl. Likewise it is possible to preserve the structural integrity of the influenza virus or its derivative when employing the process of the invention. When employing the process of the invention the influenza virus or its derivative is substantially free of DNA so that treatment with deoxyribonucleases (DNAses) can be avoided.

DETAILED DESCRIPTION OF INVENTION

Figure 1:
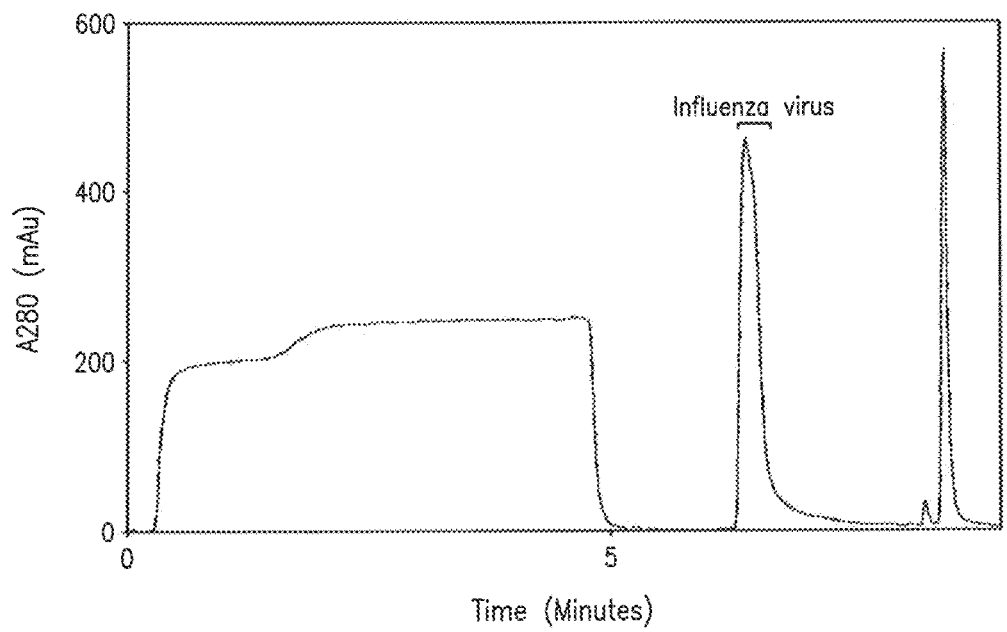
FIG. 1: Chromatogram showing the elution profile of influenza virus from three CIM® QA 8 ml tube monolithic columns connected in parallel.

The present invention deals with the development of the process for the purification of useful quantities of any influenza virus or its derivative, especially for vaccine or as viral vector use, either for laboratory or industrial scale needs. The invention avoids problems associated with existing methods of purifying influenza virus and relies on ultra filtration and chromatographic techniques which enable simple process scale up and increase productivity. Existing methods for purification of influenza virus are based on ultracentrifugation and as such are long lasting, inefficient and difficult to scale up.

According to the invention, influenza virus or its derivative is purified by providing a source having influenza virus or derivative thereof, optionally subjecting the source to a pre-purification step, followed by at least one chromatographic step on porous particles having pore sizes of at least 20 nm, membrane adsorbers, and monoliths, collecting eluting influenza virus or derivatives thereof containing fractions. Typically, the porous particles of particle sizes of about 10 μm to about 50 μm have mean pore sizes of from about 20 nm to about 500 nm or even more measured by mercury porosimetry.

In a further embodiment of the present invention at least one further chromatographic step can be performed on materials, preferably selected from the group consisting of porous particles having mean pore sizes of at least 20 nm, perfusion particles, gel-in-a-shell particles, tentacle like particles, membrane adsorbers, and monoliths.

Preferably, elution of the influenza virus is performed at mild conditions, i.e. low ionic strength of the elution buffer.

In a further embodiment of the present invention after the at least one chromatographic step on porous particles, membrane adsorbers, and monoliths an ultra filtration and/or a sterile filtration is performed.

The at least one chromatographic step on porous particles, membrane adsorbers, and monoliths may be performed with ion exchange, affinity, hydrophobic or hydrophilic interaction, size exclusion materials or combinations thereof.

In an alternative embodiment, DNA nucleases can be added before or after chromatographic step.

Any known upstream production process of influenza virus or its derivative can be used to generate the starting material for the purification process of the present invention. Suitable sources of influenza virus or its derivatives are any eukaryotic cells which support replication of the influenza virus. A preferred host cell is a mammalian host cell line which supports infection and replication of influenza virus.

According to the invention derivatives of influenza virus are in particular genetically modified influenza viruses or virus-like particles or influenza virus particles (viral vectors) delivering foreign material, such as biologically or pharmaceutically active substances, e.g. biopolymers but also small molecules. Biopolymers are in particular proteins, such as antibodies, receptors enzymes; nucleic acids (antisense nucleic acids), lipids or polysaccharides. Influenza virus-like particles can be generated e.g. from influenza virus proteins expressed in eukaryotic cells or by in vitro manipulation of influenza virus and/or molecules comprising influenza virus. Genetic manipulation of influenza virus genome may include mutations, deletions, insertions or any other manipulation of influenza virus genome. In particular the influenza virus contains at least one modification and/or deletion of the NS1 gene. Accordingly, in the process of the invention the influenza virus or derivative thereof are selected from the group consisting of influenza virus wild type, influenza virus containing modifications including substitution mutations insertions and/or deletions, and immunogenic influenza-virus-like particles.

The process of purification according to the invention is also employed in a process for the manufacturing of influenza virus comprising the steps of infecting cells with influenza virus, propagating the influenza virus in the cells, harvesting of the influenza viruses, and subjecting the harvested influenza virus or derivative thereof to the purification process of the invention. In particular, the present invention discloses and claims a process for the manufacturing or purification of influenza virus or derivative thereof comprising the steps of:
  infecting cells with influenza virus;
  propagating the influenza virus in the cells;
  harvesting of the influenza virus;
  concentrating the harvested influenza virus with a tangential flow filtration on flat sheet or hollow fiber device with 300 kDa cut off;
  subjecting the concentrated influenza virus to CIM QA monolithic column;
  subjecting the influenza virus fractions eluted from CIM QA monolithic column to Sepharose 6 FF column;
  collecting influenza virus fractions from Sepharose 6 FF column
  sterile filtration of influenza virus fractions Subject matter of the invention is also a fraction of influenza virus or derivative thereof, and a vaccine optionally comprising adjuvant, and/or pharmaceutically acceptable carriers obtainable according to the process of the invention of purification of influenza virus or derivative thereof.

Also a fraction comprising an influenza virus vector obtainable according to the invention is subject matter of the present invention. Influenza viral vector can include a heterologous nucleic acid sequence, which can be transferred from influenza viral vector to a host cell. A heterologous nucleic acid sequence may code for therapeutic protein, therapeutic nucleic acid or protein causing immune response in the organism. Methods for introducing heterologous nucleic acids into a viral vector are well known in the art.

In an embodiment of the process of the invention the pre-purification step comprises centrifugation, filtration, ultra filtration, selective precipitation, expanded bed chromatography, batch chromatography including magnetic beads or combinations thereof. Typically in the pre-purification step cell debris and other contaminants are removed from cell lysate which may be additionally adjusted to conditions optimal for further purification. In particular, the prepurification step may comprise centrifugation, filtration, and ultra filtration. Selective precipitation using polyethylene glycol or any other compound causing influenza virus or contaminants precipitation is also possible. Expanded bed chromatography and batch chromatography may be used as pre-purification steps to avoid problems such as column clogging and blocking with cell debris.

Any influenza virus can be purified by the present invention, whether it is a wild type, a mutant, or a recombinant virus or a virus-like-particle. Influenza virus can be prepared and cultivated according to methods known in the art. In an embodiment of the invention, the influenza virus or derivative thereof are selected from the group consisting of influenza virus wild type, influenza virus containing mutations including insertions and deletions, and influenza virus-like particles.

Mutations are changes in nucleic acids sequences leading to changes in amino acid sequence of protein coded by relevant gene. Deletions are mutations in which a region of the nucleic acid has been eliminated. Insertions are additional stretches of base pairs inserted into nucleic acid sequence.

Influenza-virus-like particles may be generated from influenza virus proteins expressed in different eukaryotic cells. In particular, influenza virus-like particles are immunogenic, which means that they are inducing an immune response after entering certain organism.

The methods described here permit retrieval of purified infective influenza virus particles at a high concentration in aqueous media. The methods are suitable for the preparation of laboratory or industrial quantities of any influenza virus particles.

The present invention is described in more detail but not limited to the described embodiments.

Influenza virus can be propagated and prepared by any method known in the art. The virus can be cultured in chicken eggs or cell cultures according to known procedures explained in the literature. Preferably, influenza virus is harvested from virus-infected cells, for example Vero cells. Cells may be infected at high multiplicity of infection in order to optimize yield. Any method suitable for recovering virus from infected cells may be utilised.

Cell debris can be removed by centrifugation followed by filtration. Centrifugation with or without filtration is feasible, but the combination of both methods may be the most robust method of clarification in the present invention. For smaller volumes batch centrifugation is possible but for larger volumes (over 50 L) continuous centrifugation is preferred over the batch method. The filtration step can be contemplated to additionally remove cell debris and to increase robustness of the process. Maintaining the balance between good clarification and overall yield requires investigation of a large variety of filter types. An exemplary filtration would use 0.65-0.45 μm cellulose acetate filter.

Cleared lysate containing influenza virus may then be subjected to the chromatographic technique or it may be initially concentrated using ultra filtration and subsequently purified on chromatographic columns. Ultra filtration using tangential flow is preferred and different devices can be used (e.g. Proflux and LABSCALE™ (ultrafiltration system) TFF System, both Millipore). The particular ultra filtration membrane selected will be of a size sufficient small to retain influenza virus but large enough to efficiently clear impurities. Depending on the manufacturer and membrane type, nominal molecular weight cut-offs between 100 and 1000 kDa may be appropriate (e.g. UFP-750-E-5A, GE Healthcare; BIOMAX® (ultrafiltration device) NMWC 1000, Millipore). The membrane composition may be, but it is not limited to, regenerated cellulose, polyethersulfone, polysulfone. Membranes can be flat sheets or hollow fibres. The concentration factor during ultra filtration will be a function of culture conditions, including medium, cell density and viral productivity and can be adjusted by a skilled person. Approximately, e.g. in a manner per se known, a 10 fold concentration is useful. Typical parameters that should be optimized are flux rate and trans-membrane pressure. In combination with nominal molecular weight cut-off these two parameters should enable efficient impurity removal and high virus yield at the same time. The skilled person knows how to deal with these parameters and can easily design experiments for optimization.

During ultra filtration, in particular at least 80% of host cell proteins are separated from influenza virus and can be determined in the permeate. Particularly, by using membranes with cut-offs 300 kDa, 500 kDa and 750 kDa, typically more than 90% of proteins are separated from the virus which is maintained in the retenate.

The virus may be further purified based on its surface charge. As noted, cleared lysate or concentrate prepared by ultra filtration may be purified by ion exchange chromatography. Cleared lysate or concentrate can be loaded directly onto the column or can be adjusted to certain conditions in order to achieve maximum efficiency of the method. Different buffer solutions can be used for adjustment and for ion exchange chromatographic step. Examples of buffers that can be used in the ion exchange chromatographic step include phosphate, phosphate citrate, Tris-HCl, MOPS, HEPES, and the like. Buffers can also be formulated incorporating a stabilizing agent, e.g. disaccharides such as sucrose.

Ion exchange chromatographic steps allow for the use of a wide variety of commercially available chromatographic materials known to be useful in fractionation of biological materials. Chromatographic supports of different basic material (natural and synthetic polymers) may be used in the invention. These basic materials may be of different shape, including particle supports, membranes and monoliths. Anion exchange chromatography may be performed by utilizing various functional groups, including, but not limited to, DEAE (diethyl amine), EDA (ethylene diamine) and QA (quaternary amine). These functional groups may be attached to any suitable resin useful in the present invention. Cation exchange chromatography also may be used for influenza virus purification, including but not limited to, $SO_3$ (sulfonyl) and CM (carboxymethyl) functional groups attached to any suitable resin.

Cleared lysate or concentrate prepared by ultra filtration is adjusted to conditions under which influenza virus may be bound to positively (anion) or negatively (cation) charged functional groups on the surface of the chromatographic support. Subsequently, bound virus particles are eluted from chromatographic support using increased ionic strength of the buffer.

Preferably, a monolithic support based on poly(glycidyl methacrylate-co-ethylene dimethacrylate) matrix, with quaternary amine (QA) functional groups (e.g. CIM® QA monolithic column) is used in the ion exchange chromatography step of the process of the present invention. Cleared cell lysate or ultra filtration concentrate may be adjusted to conditions which enable influenza virus binding to the positively charged functional groups of the chromatographic support. Preferably, buffer with high buffer capacity at pH value between 7 and 8 is used for this step (e.g. Tris, HEPES). Under such conditions negatively charged virus particles are bound to positively charged functional groups on the surface of monolithic support. Elution of the virus particles is achieved e.g. by the increasing ionic strength of the buffer, in particular using sodium chloride.

This anion exchange chromatography step may be used for DNA removal as well. Since host cell DNA is negatively charged it will be bound to functional groups on the surface of chromatographic support. DNA is eluted from the anion exchange support at higher ionic strength compared to influenza virus. Material eluted from an anion exchange column at ionic strength suitable for influenza virus elution will not contain host cell DNA. As a consequence the treatment of the influenza virus containing solution with deoxiribonuclease (e.g. Benzonase, Merck) is in the preferred embodiment not needed. On the contrary, it is preferred that no deoxiribonuclease is used in the present invention, since DNA fragmentation and size reduction can increase DNA content in the final influenza virus pool, as well deoxiribonuclease has to be removed from the final product intended for human use.

Influenza virus sample eluted from anion exchange column may be further purified on the basis of its size. Preferably, the buffer in which virus was eluted from the anion exchange column, is exchanged more or less at the same time. In the process of the invention, size exclusion chromatography and tangential flow filtration are preferred. Both methods enable impurity removal and buffer exchange at almost the same time.

Tangential flow ultra filtration is a method which may be used to remove residual protein and nucleic acids as well as for exchanging working buffer into a final formulation buffer. Ultra filtration using tangential flow is preferred and different devices can be used (e.g. Proflux and LAB-SCALE™ (ultrafiltration system) TFF System, both Millipore). The particular ultra filtration membrane selected will be of a filter pore size sufficient small to retain influenza virus but large enough to allow penetration of impurities. Depending on the manufacturer and membrane type, nominal molecular weight cut-offs between 100 and 1000 kDa may be appropriate (e.g. UFP-750-E-5A, GE Healthcare; BIOMAX® (ultrafiltration device) NMWC 1000, Millipore). The membrane composition may be, but it is not limited to, regenerate cellulose, polyethersulfone, polysulfone. Membranes can be of flat sheet or hollow fibre type. Main parameters that must be optimized are flux rate and trans-membrane pressure. In combination with nominal molecular weight cut-off these two parameters will enable efficient purification and buffer exchange and high virus yield.

Size exclusion chromatography (SEC) also enables simultaneous impurity removal and buffer exchange. SEC allow for the use of wide variety of commercially available chromatographic materials known to be useful in SEC of biological materials. A chromatographic support of different basic materials (natural and synthetic polymers) may be used in the invention. SEC supports may have different particle and pore size. Preferably, SEC supports with pore sizes which results in the influenza virus particles being completely excluded out of the pores of the resin particles and therefore eluting in the void volume of the column, are used in this invention. At the same time resin particle pore sizes should enable entrance of the impurities resulting in the longer elution volume if compared to the influenza viral particle allowing further purification of the product. In particular SEC support, such as SEPHAROSE® (chromatography resin) FF (GE Healthcare), FRACTOGEL® (chromatography resin) EMD BioSEC (Merck kGaA) and TOYOPEARL® (chromatography resin) HW-75 (Tosoh Bioscience), in a group separation mode may be used for influenza virus purification. Buffers that can be used in a SEC step include phosphate, phosphate citrate, and other biologically compatible buffers. Buffers can also be formulated with a stabilizing agent, e.g. disaccharides such as sucrose and/or detergent. Compounds preventing ion interactions between SEC resin and influenza virus, such as sodium chloride may be also added to the buffer.

As an additional step sterile filtration may be performed to eliminate bioburden. Therefore SEC eluate or final retentate from the ultra filtration step may be filtered through a 0.22 μm filter. The filter may be constructed from various materials, which may include but are not limited to polypropylene, cellulose, cellulose esters, nylon, polyethersulfone, or any other material which is consistent with low unspecific influenza virus binding. The filter may have a single membrane layer or more than one layer or may incorporate a prefilter of the same or different material. The filtrated influenza virus can be held frozen or kept at approximately 4° C. for subsequent manipulation.

The present invention describes an influenza virus purification process composed of ultra filtration and chromatographic methods. Scale up of ultra filtration and chromatographic methods as such are well known in the art. The disclosed invention can be used on a laboratory scale or can be transferred to pilot or industrial scale using previously described methods. Of course last step, namely sterile filtration, or last two steps, namely sterile filtration and SEC (or ultra filtration) can be omitted when there is no strict demand for high purity of the influenza viral particle (this especially applies for the laboratory scale applications).

EXAMPLES

Example 1

This example demonstrates the preferred influenza virus purification method of the present invention using tangential flow filtration, anion exchange chromatography, size exclusion chromatography and sterile filtration followed each other in this order.

Influenza virus reassortment of A/PR/8/34 Mt. Sinai with deletion in NS1 gene and IVR-116 was cultivated on Vero cells in GIBCO®OPTIPRO™ (cell culture medium) SFM medium. Approximately 15000 mL of cell lysate was clarified by centrifugation at 2400 rpm at room temperature for 10 minutes. The supernatant was collected and filtered through a Sartobran P 500 cm² capsule filter with a cellulose acetate membrane, 0.65-0.45 μm.

The filtrate was concentrated by tangential flow filtration using Proflux system (Millipore) and hollow fibre TFF cartridge with 750 kDa nominal cut-off and 0.12 m² area (GE Healthcare, UFP-750-E-5A). The trans-membrane pressure was 0.2 to 0.3 bar. The final volume of concentrate was 1400 ml.

The concentrate was further purified using three CIM® QA 8 ml tube monolithic columns connected in parallel (BIA Separations), having a total bed volume of 24 ml. The following buffers were used:

Buffer A: 50 mM HEPES (pH=7.5), Buffer B: 50 mM HEPES/0.3M NaCl (pH=7.5), Buffer C: 50 mM HEPES/ 2.0M NaCl (pH=7.5).

The flow rate was 300 ml per minute. Before use, CIM® QA 8 ml tube monolithic columns were sanitised with 40 column volumes of 1M NaOH (2 hours contact time). Equilibration was done with 20 column volumes of Buffer C followed by 20 column volumes of Buffer A. 1350 ml of concentrate containing described influenza virus was loaded on the column and after that column was washed with 20 column volumes of Buffer A. Influenza virus was eluted with Buffer B and 115 ml of eluate was collected. Remaining impurities bound to the column were eluted with Buffer C (FIG. 1). Finally, columns were sanitised with 40 column volumes of 1M NaOH (2 hours contact time).

Figure 2:
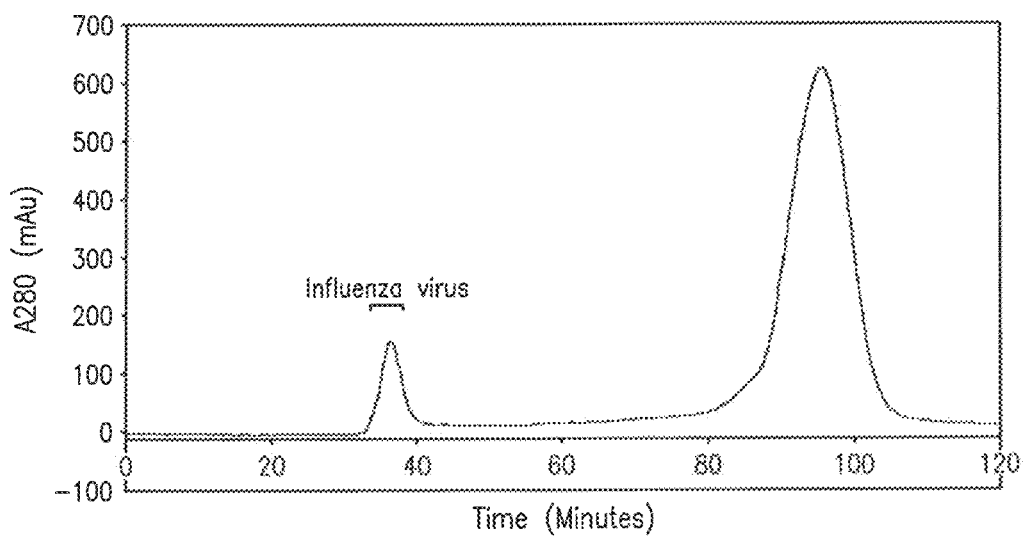
FIG. 2: Chromatogram showing the elution profile of influenza virus from SEPHAROSE® (chromatography resin) 6 Fast Flow (Index 70/90, 2000 ml).

The size exclusion chromatography was used as a final purification and buffer exchanging step. Index 70/950 column was filled with SEPHAROSE® (chromatography resin) Fast Flow (GE Healthcare, 17-0159-05) to 2000 ml bed volume (N: 4664/m). SPG buffer (0.218 M sucrose, 0.0038 M KH2PO4, 0.0072 M K2HPO4, 0.0049 K-glutamate pH 8.0±0.2) was used and flow rate was 20 ml/min. The column was sanitised with 5 column volumes of 1M NaOH (2 hours contact time) and equilibrated with 5 column volumes of SGP buffer. 40 ml of CIM® QA eluate (2% of the columns volume) was loaded on the column. An influenza virus containing fraction was eluted in void volume of the column and collected in 128 ml (FIG. 2).

The collected fractions were tested for host cell protein content (FIG. 3), DNA size (FIG. 4), protein content by BCA method, DNA content by the Picogreen method, and virus titer was determined by using the TCID50 assay (Table 1). The results confirm that the described process enables a fast (single day) and efficient purification of influenza virus.

Figure 3:
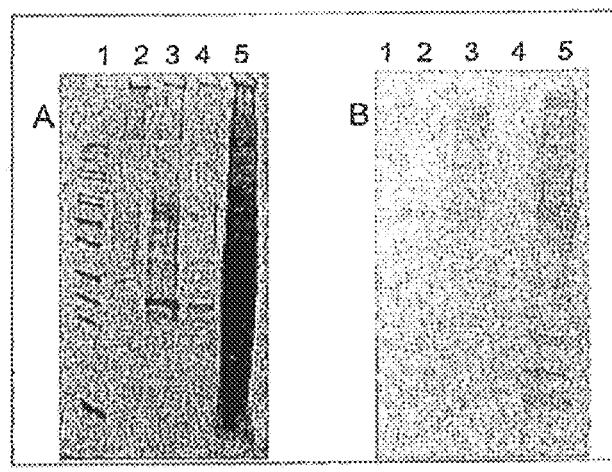
FIG. 3: SDS-PAGE and Western blot analysis of fractions purified on CIM® QA monolithic columns and SEPHAROSE® (chromatography resin) Fast Flow.

FIG. 3 shows SDS-PAGE and Western blot analysis of fractions purified on CIM® QA monolithic columns and SEPHAROSE® (chromatography resin) Fast Flow.

A: PAGE Gold Tris-Glycine gel (10-20%) (Cambrex) stained with a Silver staining kit PlusOne (GE Healthcare). Line 1: PageRuler Protein Ladder (Fermentas, 200, 150, 120, 100, 85, 70, 60, 50, 40, 30, 25, 20, 15, 10 kDa); Line 2: TFF concentrate; Line 3: CIM® QA eluate; Line 4: SEC eluate; Line 5: Vero host cell protein.

B: Detection of Vero host cell proteins with rabbit polyclonal antiserum and anti-rabbit HRP conjugated antibodies. Line 1: PageRuler Protein Ladder (Fermentas, 200, 150, 120, 100, 85, 70, 60, 50, 40, 30, 25, 20, 15, 10 kDa); Line 2: TFF concentrate; Line 3: CIM® QA eluate; Line 4: SEC eluate; Line 5: Vero host cell protein.

Figure 4:
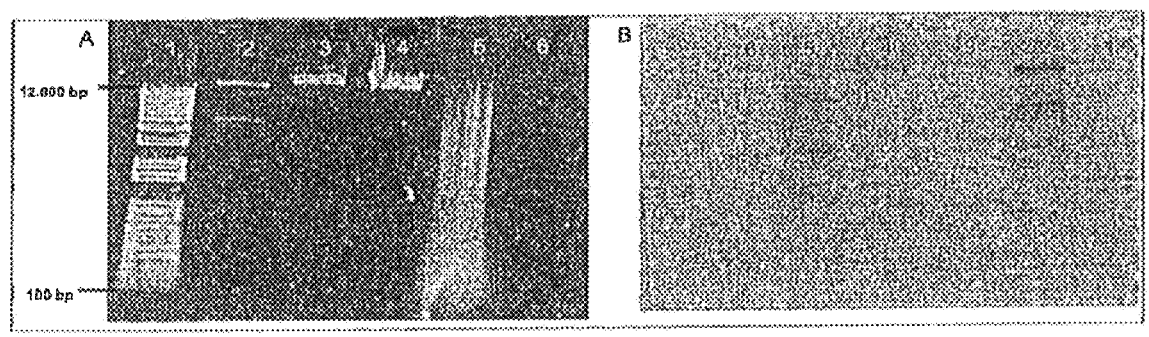
FIG. 4: Southern blot analysis of fractions purified on CIM® QA monolithic column.
Figure 5:
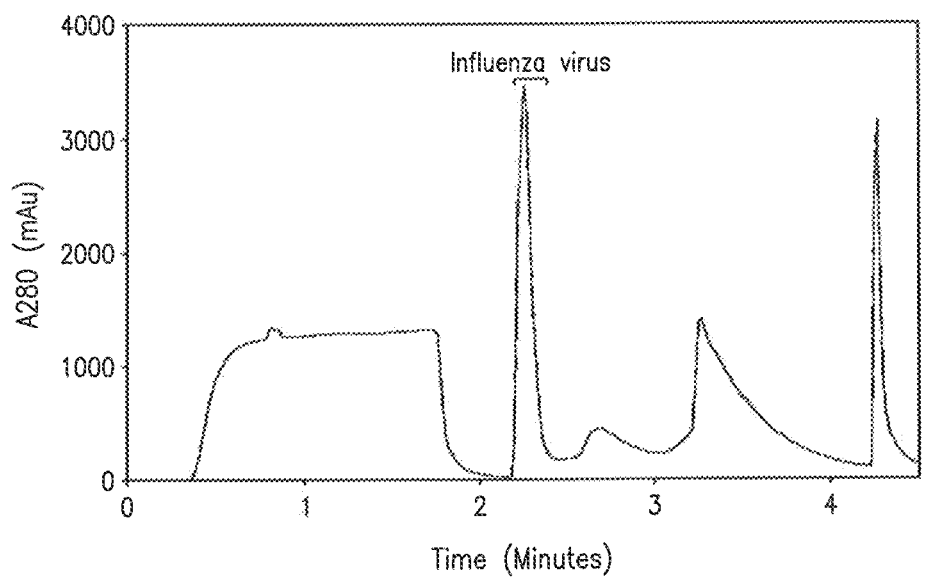
FIG. 5: Chromatogram showing the elution profile of influenza virus from CIM® DEAE disk monolithic column.
Figure 6:
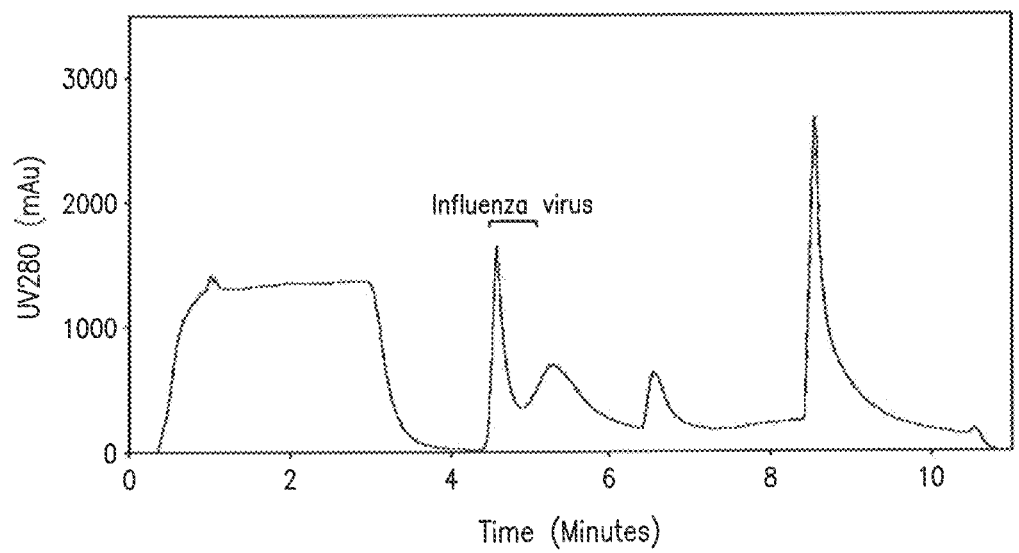
FIG. 6: Chromatogram showing the elution profile of influenza virus from CIM® QA disk monolithic column.
Figure 7:
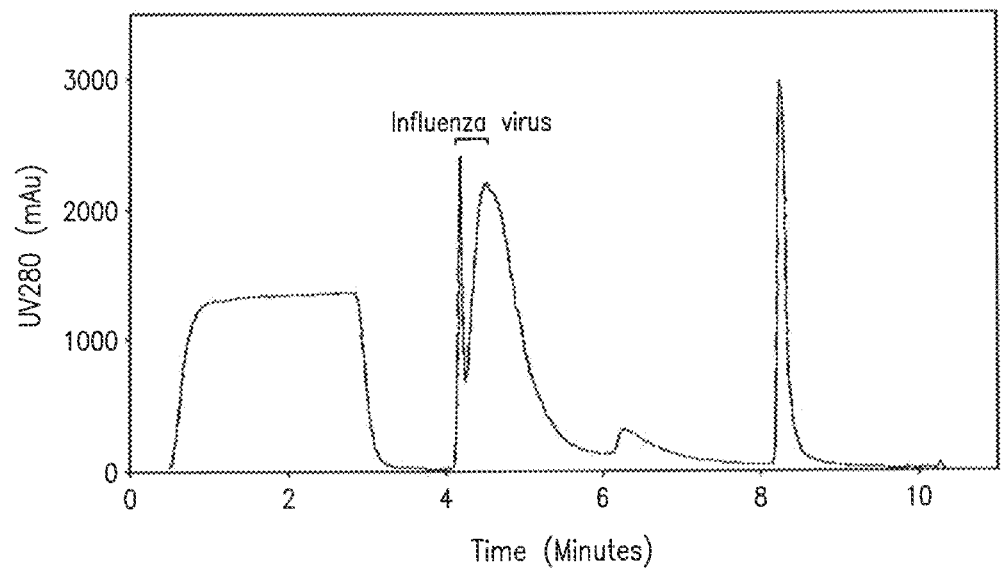
FIG. 7: Chromatogram showing the elution profile of influenza virus from CIM® EDA disk monolithic column.
Figure 8:
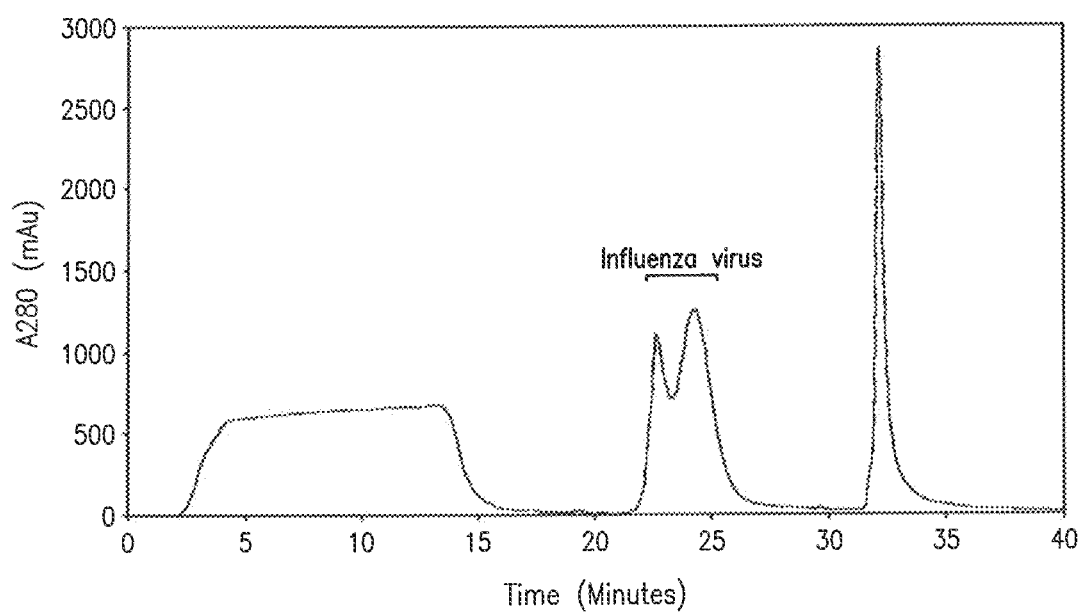
FIG. 8: Purification of influenza virus on Q SEPHAROSE® (chromatography resin) XL Virus.
Figure 9:
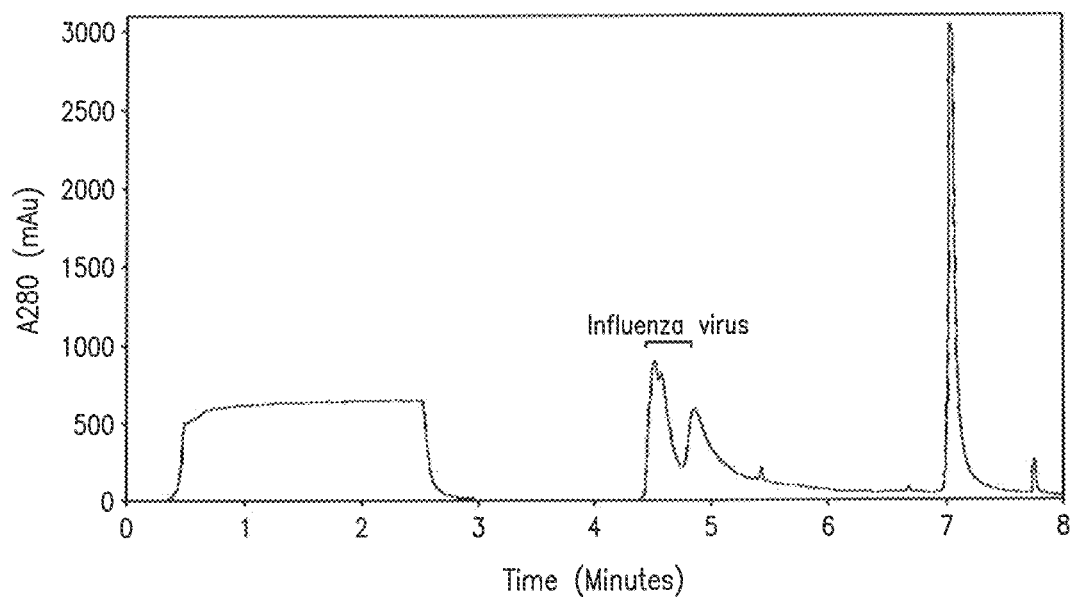
FIG. 9: Purification of influenza virus on CIM® QA disk monolithic columns.
Figure 10:
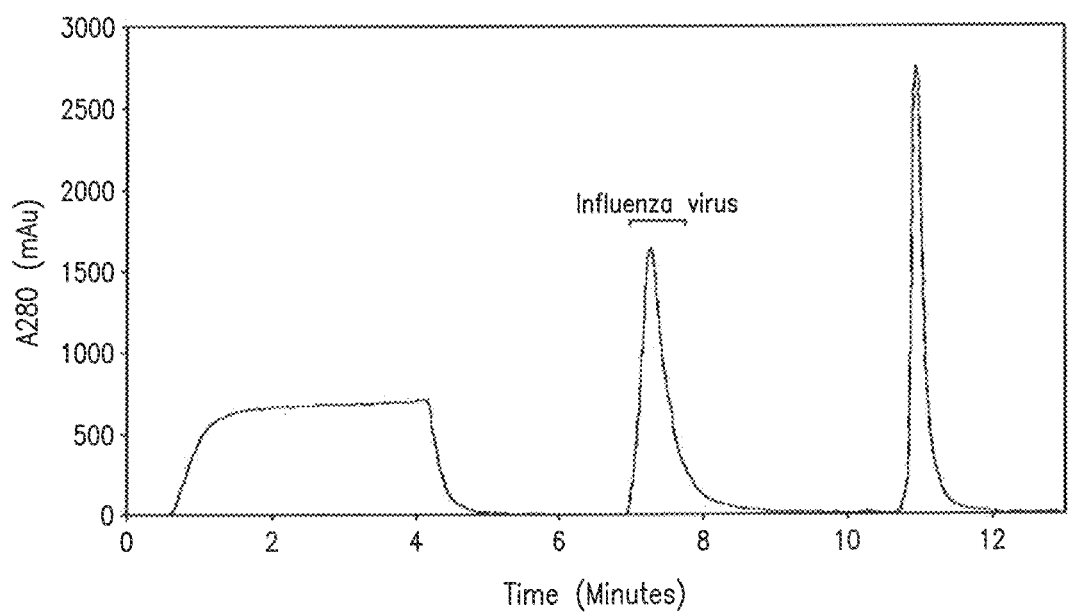
FIG. 10: Purification of influenza virus on MUSTANG® (membrane adsorber) Q membrane.
Figure 11:
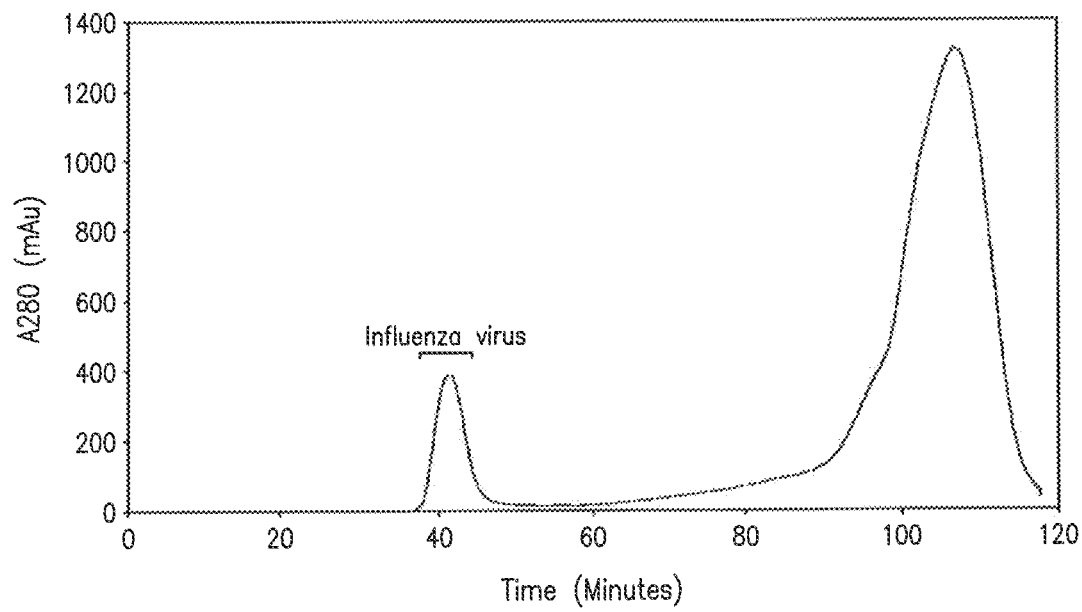
FIG. 11: Elution profile of influenza virus from SEPHAROSE® (chromatography resin) Fast Flow.
Figure 12:
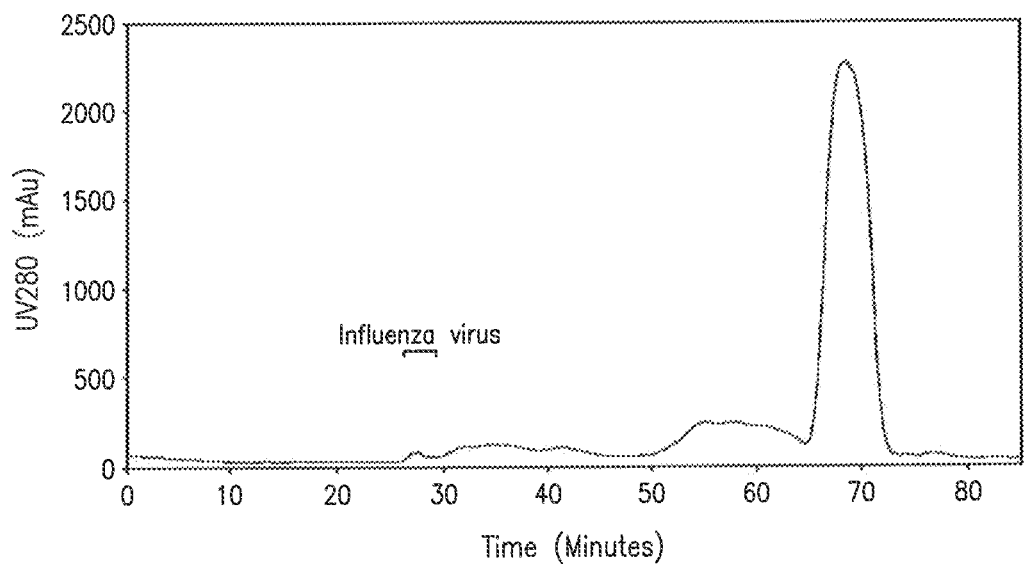
FIG. 12: Elution profile of influenza virus from FRACTOGEL® (chromatography resin) BioSEC.
Figure 13:
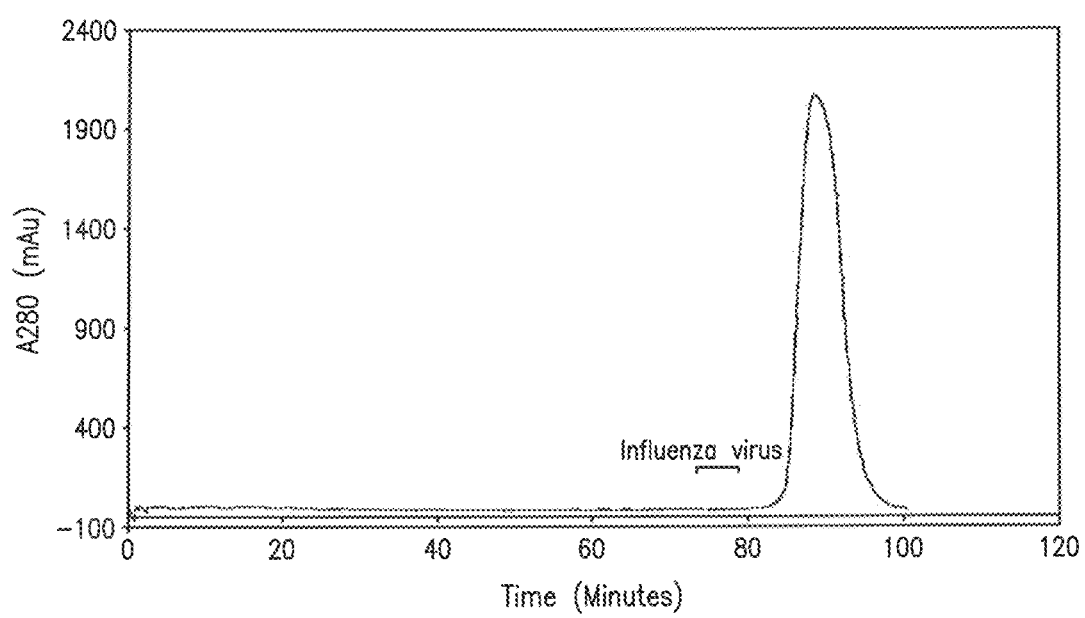
FIG. 13: Elution profile of influenza virus from TOYOPEARL® (chromatography resin) HW-75.

FIG. 4 depicts Southern blot analysis of fractions purified on CIM® QA monolithic column A: Agarose gel electrophoresis stained by ethidium bromide. Line 1: DNA Standard (1 kb Plus DNA Ladder, Invitrogen); Line 2: DNA molecular weight marker III, DIG labelled (Roche); Line 3: Vero cells DNA; Line 4: Vero cells DNA; Line 5: TFF concentrate; Line 6: CIM® QA eluate B: Southern blot and detection of Vero cells DNA with probe labeled with digoksigenin (DIG High Prime DNA Labelling and detection Starter Kit II). Line 1: DNA Standard (1 kb Plus DNA Ladder, Invitrogen); Line 2: DNA molecular weight marker III, DIG labelled (Roche); Line 3: Vero cells DNA; Line 4: Vero cells DNA; Line 5: TFF concentrate; Line 6: CIM® QA eluate.

TABLE 1

Analyses of samples collected at different steps of purification process

| | Virus titer (TCID50/ml) | DNA (ng/ml) | Proteins (μg/ml) |
|---|---|---|---|
| Harvest | 1.0E+07 | — | — |
| Concentrate | 1.0E+08 | 1510 | 950 |
| CIM QA elutio | 6.3E+08 | 1.5 | 240 |
| SEC elution | 1.5E+08 | 2.4 | 17 |

Example 2

In this example three different anion exchange functional groups are compared. The example illustrates that different anion exchange functional groups can be used for the purification of influenza virus particles.

Influenza virus reassortment of A/PR/8/34 Mt. Sinai with deletion in NS1 gene and IVR-116 was cultivated on Vero cells in GIBCO®OPTIPRO™ (cell culture medium) SFM medium. The cell lysate was clarified by centrifugation at 2400 rpm at room temperature for 10 minutes. The supernatant was collected and concentrated by tangential flow filtration using a LABSCALE™ (ultrafiltration system) TFF system (Millipore) and a PELLICON® (ultrafiltration device) BIOMAX® (ultrafiltration device) 300 kDa cut-off membrane (Millipore, PXB3 00C 50). The concentrate was used for comparison of three CIM® disks monolithic columns: CIM® QA disk, CIM® DEAE disk, and CIM® EDA disk monolithic column (BIA Separations). Following buffers were used:

Buffer A: 50 mM HEPES (pH=7.5), Buffer B: 50 mM HEPES/0.3M NaCl (pH=7.5), Buffer C: 50 mM HEPES/1.5M NaCl (pH=7.5).

On each column 6 ml of concentrate was loaded and the virus was eluted in a step gradient using Buffer B. The flow rate on CIM® DEAE disk was 6 ml/min (FIG. 5), and on CIM® QA disk (FIG. 6) and CIM® EDA disk (FIG. 7) 3 ml/min. The eluted fractions were analysed for influenza virus content by hemagglutination assay and the virus yield was calculated (Table 2). Results confirm that different anion exchange functional groups can be used for influenza virus purification although the strong anion exchange (QA) looks to be the most suitable.

TABLE 2

Influenza virus recovery on different anion exchange CIM ® disks monolithic column

| | Virus yield (%) |
|---|---|
| CIM ® DEAE | 25 |
| CIM ® QA | 50 |
| CIM ® EDA | 25 |

Example 3

In this example three different types of chromatographic support are compared. The example illustrates that the porous particle support, membranes and monoliths can be used for the purification of influenza virus.

Influenza virus reassortment of A/PR/8/34 Mt. Sinai with deletion in NS1 gene and IVR-116 was cultivated on Vero cells in GIBCO®OPTIPRO™ (cell culture medium) SFM medium. The cell lysate was clarified by centrifugation at 2400 rpm at room temperature for 10 minutes. The supernatant was collected and concentrated by a tangential flow filtration using LABSCALE™ (ultrafiltration system) TFF system (Millipore) and a PELLICON® (ultrafiltration device) BIOMAX® (ultrafiltration device) 300 kDa cut-off membrane (Millipore, PXB3 00C 50). The concentrate was used for the comparison of three different chromatographic supports: CIM® QA disk monolithic column (BIA Separations), Q SEPHAROSE® (chromatography resin) XL virus licensed (GE Healthcare), and MUSTANG® (membrane adsorber) Q coin (Pall). The following buffers were used:

Buffer A: 50 mM HEPES (pH=7.5), Buffer B: 50 mM HEPES/0.3M NaCl (pH=7.5), Buffer C: 50 mM HEPES/1.5M NaCl (pH=7.5).

An aliquot of a concentrate containing influenza virus was applied to the column Q SEPHAROSE® (chromatography resin) XL, virus licensed (1 ml bed volume), at a flow rate of 1 ml/min. The virus was eluated from the column in step gradient of Buffer B. Remaining impurities including host cell DNA were eluted using Buffer C (FIG. 8). Another aliquot of the virus concentrate was applied to a Mustang Q coin (0.35 ml bed volume) at flow rate of 3 ml/min and yet another aliquote to a CIM® QA disk monolithic column (0.34 ml bed volume) at 6 ml/min. From all units the virus was eluated in step gradient of Buffer B and while two peaks were observed in a CIM QA (FIG. 9) chromatogram, only one is present in a Mustang Q coin chromatogram (FIG. 10). The collected fractions were analysed for an influenza virus content by the TCID50 assay and for host cell DNA presence (Picogreen assay) (Table 3).

TABEL 3

Analysis of influenza virus containg fractions eluted from different anion exchange supports

| | Virus yield (%) | DNA (ng/ml) |
|---|---|---|
| Q Sepharose XL | 24.1 | <10 |
| Mustang Q | 39.9 | <10 |
| CIM QA | 42.3 | <10 |

Example 4

In this example three different types of size exclusion chromatographic (SEC) supports are compared. The example illustrates that different SEC supports can be used for influenza virus purification.

Influenza virus reassortment of A/PR/8/34 Mt. Sinai with deletion in NS1 gene and IVR-116 was cultivated on Vero cells in GIBCO®OPTIPRO™ (cell culture medium) SFM medium. The cell lysate was clarified by centrifugation at 2400 rpm at room temperature for 10 minutes. Supernatant was collected and concentrated by tangential flow filtration using a LABSCALE™ (ultrafiltration system) TFF system (Millipore) and a PELLICON® (ultrafiltration device) BIOMAX® (ultrafiltration device) 300 kDa cut-off membrane (Millipore, PXB3 00C 50). The concentrate was further purified on a CIM® QA monolithic column (BIA Separations) as described in Example 1. The influenza virus eluted from the CIM® QA monolithic column in 50 mM HEPES/0.3M NaCl (pH=7.5) was used for comparison of SEC supports. SEPHAROSE® (chromatography resin) FF (GE Healthcare), TOYOPEARL® (chromatography resin) HW-75 (Tosoh Bioscience), and FRACTOGEL® (chromatography resin) EMD BioSEC (Merck) were packed in a HR 16/50 column to 100 ml bed volume and compared for their separation profile and recovery. For all experiments SPG buffer (0.218 M sucrose, 0.0038 M $KH_2PO_4$, 0.0072 M $K_2HPO_4$, 0.0049 K-glutamate pH 8.0±0.2) was used.

The influenza virus containing fraction eluting from the CIM QA monolithic column was loaded on different SEC supports at 1 ml/min (30 cm/h). The collected fractions were analysed for an influenza virus content by hemagglutination assay and the virus yield was calculated (Table 4). From SEPHAROSE® (chromatography resin) FF (FIG. 11) and FRACTOGEL® (chromatography resin) EMD BioSEC (FIG. 12) the influenza virus was eluted in the void volume of the column, and on TOYOPEARL® (chromatography resin) HW-75 (FIG. 13) the virus interacted with the support and eluted later.

TABLE 4

Influenza virus recovery rate on different SEC supports

| | Recovery |
|---|---|
| Sepharose 6 FF | 40.0 |
| Toyopearl HW-75 | 46.9 |
| Fractogel ® EMD BioSEC | 54.5 |

Example 5

In this example four different types of chromatographic support are compared with regard to dynamic binding capacity for influenza virus particles. The example illustrates the difference between membranes, monoliths, and particles on one side compared to material according to EP-A-0 171 086—represented by CELLUFINE® (chromatography resin) sulphate—on other side.

Influenza virus reassortment of A/PR/8/34 Mt. Sinai with deletion in NS1 gene and IVR-116 was cultivated on Vero cells in GIBCO®OPTIPRO™ (cell culture medium) SFM medium. The cell lysate was clarified by centrifugation at 2400 rpm at room temperature for 10 minutes. The supernatant was collected and concentrated by a tangential flow filtration using LABSCALE™ (ultrafiltration system) TFF system (Millipore) and a BIOMAX® (ultrafiltration device) 300 kDa cut-off membrane (Millipore, PXB3 00C 50). The concentrate was used for the comparison of four different chromatographic supports: CIM® QA disk monolithic column (BIA Separations), Q SEPHAROSE® (chromatography resin) XL virus licensed (GE Healthcare), MUSTANG® (membrane adsorber) Q coin (Pall) and CELLUFINE® (chromatography resin) sulfate (Chisso). The following buffers were used: Buffer A: 50 mM HEPES (pH=7.5), Buffer B: 50 mM HEPES/0.5M NaCl (pH=7.5), Buffer C: 50 mM HEPES/2.0M NaCl (pH=7.5).

The concentrate was pumped through each column at defined flow rate and fractions were collected and analysed for influenza virus presents. Dynamic binding capacity for each support was calculated at break-through (Table 5). 10 to 100 fold difference in dynamic binding capacity exist between particle supports (CELLUFINE® (chromatography resin) sulfate and Q SEPHAROSE® (chromatography resin) XL) on one and monoliths and membranes (CIM QA and MUSTANG® (membrane adsorber) Q) on the other side. Such differences may significantly influence design of purification process.

TABLE 5

Dynamic binding capacities of different supports for Influenza virus

| | Bed volume (ml) | Flow rate (ml/min) | Flow rate (CV/min) | Dynamic binding capacity (TCID50/ ml of support) |
|---|---|---|---|---|
| Mustang Q | 0.35 | 3.5 | 10.0 | 2.0E+10 |
| CIM QA | 0.34 | 6.0 | 17.6 | 2.0E+10 |
| Celufine sulphate | 0.35 | 0.5 | 1.4 | 2.7E+08 |
| Q Sepharose XL | 0.70 | 0.5 | 0.7 | 1.0E+09 |

Example 6

In this example four different types of chromatographic support are compared. The example illustrates that particle support, membranes and monoliths can be used for the purification of influenza virus but a difference significantly influencing the purification process design can be observed.

Influenza virus reassortment of A/PR/8/34 Mt. Sinai with deletion in NS1 gene and IVR-116 was cultivated on Vero cells in GIBCO®OPTIPRO™ (cell culture medium) SFM medium. The cell lysate was clarified by centrifugation at 2400 rpm at room temperature for 10 minutes. The supernatant was collected and concentrated by a tangential flow filtration using LABSCALE™ (ultrafiltration system) TFF system (Millipore) and a PELLICON® (ultrafiltration device) BIOMAX® (ultrafiltration device) 300 kDa cut-off membrane (Millipore, PXB3 00C 50). The concentrate was used for the comparison of four different chromatographic supports: CIM® QA disk monolithic column (BIA Separations), Q SEPHAROSE® (chromatography resin) XL virus licensed (GE Healthcare), MUSTANG® (membrane adsorber) Q coin (Pall) and CELLUFINE® (chromatography resin) sulfate (Chisso). The following buffers were used: Buffer A: 50 mM HEPES (pH=7.5), Buffer B: 50 mM HEPES/0.5M NaCl (pH=7.5), Buffer C: 50 mM HEPES/ 2.0M NaCl (pH=7.5).

Aliquots of a concentrate containing influenza virus were applied to columns Q SEPHAROSE® (chromatography resin) XL, virus licensed (0.34 ml bed volume) and CELLUFINE® (chromatography resin) sulfate (0.35 ml bed volume), at a flow rate of 0.5 ml/min. Another aliquot of the virus concentrate was applied to a MUSTANG® (membrane adsorber) Q coin (0.35 ml bed volume) at flow rate of 3.5 ml/min and yet another aliquot to a CIM® QA disk monolithic column (0.34 ml bed volume) at 3 ml/min. The virus was eluted from all columns in step gradient of Buffer B. Remaining impurities including host cell DNA were eluted using Buffer C. The collected fractions were analyzed for influenza virus content by TCID50 and hemagglutination assay, for host cell DNA content by Picogreen assay and for protein content by BCA assay (Table 6). Fractions eluted from tested supports differ in virus, DNA and protein content. The highest virus titer and virus recovery was achieved on CIM QA and this fraction has the highest protein and low DNA concentration. Fraction eluted from Celufine sulfate has the lowest virus titer and lowest virus recovery, and the highest DNA concentration.

TABLE 6

Analysis of influenza virus containing fraction eluted from different anion exchange supports with buffer B

| | Virus | | | | DNA | |
|---|---|---|---|---|---|---|
| Column | TCID50/ ml | Yield (%) | HA | Yield (%) | ng/ml | DNA removal (%) |
| CIM QA | 1.12E+08 | 54.00 | 256 | 77.00 | 64.20 | 95.50 |
| Coin Q | 5.80E+07 | 35.30 | 64 | 24.00 | 63.00 | 95.10 |
| Q Sepharose XL | 9.60E+07 | 34.50 | 128 | 28.00 | 105.40 | 94.50 |
| Celufine sulfat | 5.22E+07 | 26.50 | 32 | 21.00 | 114.50 | 91.60 |

REFERENCES

Prasak Nayak D, Lehmann S, Reichl U. Downstream processing of MDCK cell-derived equine influenza virus. J Chromatograp B, 823 (2005), 75-81.

Pepper D S. A chromatographic procedure for the purification of influenza virus. J Gen Virol, 1 (1967), 49-55.

Wallis C, Homma A, Melnic J L. Concentration and purification of influenza virus on insoluble polyelectrolytes. Appl Microbiol, 23 (1972), 740-744.

Heyward J T, Klinas R A, Stapp M D, Obijeski J F. The rapid concentration and purification of influenza virus from allantoic fluid. Arch Virol, 55 (1977), 107-119.

Sagar M G, Hanssen H, Gerba C P. Simple method for the concentration of influenza virus from allantoic fluid on microporous filters. Appl Environ Microbiol 39 (1980), 500-504.

Reimer C B, Baker R S, Newlin T E, Havens M L. Influenza virus purification with the zonal ultracentrifuge. Science 152 (1966), 1379-1381.

Veeraraghavan N, Sreevalsan T., Evaluation of some methods of concentration and purification of influenza virus. Bull World Health Organ 24 (1961), 695-702.

The invention claimed is:

1. A process for the purification of infective influenza virus selected from the group consisting of influenza virus wild type and influenza virus containing mutations, comprising the steps of:

providing a source containing the influenza virus in an infectious state;

subjecting the source to a pre-purification step selected from the group consisting of centrifugation, tangential flow filtration ultrafiltration, selective precipitation, expanded bed chromatography, batch chromatography utilizing magnetic beads and combinations thereof;

followed by more than one anion exchange chromatographic step on chromatographic anion exchange monoliths arranged in parallel and having positively charged functional groups on the monolith surface and selected from the group consisting of monoliths having ethylene diamine (EDA) groups, monoliths having quaternary amine (QA) groups, and monoliths having diethylaminoethyl (DEAE) groups, each chromatographic step utilizing, independently, a loading buffer having a pH of 7-8 and an elution buffer containing about 0.3M-1M NaCl, thereby, obtaining a fraction with infective virus in a yield of at last about 40%; and subjecting the obtained fraction to size exclusion chromatography;
with the proviso that sulfuric ester of cellulose and sulfuric ester of cross-linked polysaccharides are excluded.

2. The process of claim 1, wherein the influenza virus in an infectious state contains at least one modification and/or deletion of the NS1 gene.

3. A process for the purification or manufacturing of infective influenza virus, comprising the steps of:
infecting cells with influenza virus;
propagating the infectious influenza virus in the cells;
harvesting the infectious influenza viruses; and
subjecting the infectious harvested influenza virus to the purification process according to claim 1.

4. A process of the purification of infective influenza virus, comprising the steps of:
infecting cells with influenza virus;
propagating the infectious influenza virus in the cells;
harvesting the infectious influenza virus;
subjecting the concentrated infectious influenza virus to the purification process according to claim 1, wherein the pre-purification step comprises concentrating the infectious harvested influenza virus by tangential flow filtration on a flat sheet or hollow fiber membrane with a 300 kDa cut off, and with the monoliths having positively charged functional groups comprising a poly (glycidyl methacrylate-co-ethylene dimethacrylate) matrix having quaternary amine (QA) functional groups;
sterile filtration of infectious influenza virus fractions eluted from the size exclusion chromatography.

5. An infectious influenza virus obtained according to the process of claim 1.

6. A vaccine comprising influenza virus purified according to the process of claim 1.

7. The vaccine of claim 6 further comprising an adjuvant, a pharmaceutically acceptable carrier, or both.

8. A vaccine comprising an influenza virus purified according to the process of claim 4.

9. The process of claim 1, wherein, after the at least one anion exchange chromatographic step, an ultrafiltration and/or sterile filtration is performed.

10. A vaccine comprising an influenza virus purified according to the process of claim 3.

* * * * *